United States Patent [19]

Abou-Gharbia

[11] Patent Number: 4,663,456

[45] Date of Patent: May 5, 1987

[54] 2-(SUBSTITUTED PIPERAZINYLALKYL)β-CARBOLINES USEFUL IN TREATMENT OF PSYCHOLOGICAL DISORDERS

[75] Inventor: Magid A. Abou-Gharbia, Wilmington, Del.

[73] Assignee: American Home Products Corporation, New York, N.Y.

[21] Appl. No.: 776,338

[22] Filed: Sep. 16, 1985

[51] Int. Cl.$^4$ .......................................... C07D 403/14
[52] U.S. Cl. .................................. 544/295; 544/298; 544/319; 544/320; 544/328; 544/331; 544/333; 544/334; 544/357; 544/361; 544/375; 544/396
[58] Field of Search ............... 544/298, 319, 328, 357, 544/361, 396, 295, 320, 328, 331, 333, 334, 375; 514/253

[56] References Cited

U.S. PATENT DOCUMENTS 4,427,679  1/1984  Welch et al. ...................... 544/361
4,575,508  3/1986  Steiner et al. ...................... 544/361

FOREIGN PATENT DOCUMENTS 22853    10/1964  Japan.
1058193   2/1967  United Kingdom ................ 544/361

OTHER PUBLICATIONS

Jilek et al., Chem. Abst. 54, 24798.
Koretskaya et al., Chem. Abst. 51, 15535.
Derwent Abstract 20,387 (Jap. 2713/66;2/21/66).

*Primary Examiner*—Donald G. Daus
*Assistant Examiner*—Cecilia Shen
*Attorney, Agent, or Firm*—Richard K. Jackson

[57] ABSTRACT

The β-carbolines N-substituted in 2-position with a piperidinyl alkyl group are antipsychotic agents and anxiolytic agents with minimal extrapyramidal side effects, useful in the treatment of psychological disorders such as paranoia and schizophrania as well as general states of anxiety.

6 Claims, No Drawings

2-(SUBSTITUTED PIPERAZINYLALKYL)β-CARBOLINES USEFUL IN TREATMENT OF PSYCHOLOGICAL DISORDERS

BACKGROUND OF THE INVENTION

Beta-carbolines possessing central nervous system activity are known. Japanese Patent No. 22,853 discloses such compounds as sedatives and as possessing antihypertensive activity. Derwent 20,387 abstracts Japanese Pat. No. 2,713, which indicates that beta-carbolin-1-one derivatives act as central nervous system depressants as well as possessing antihistaminic activity.

DESCRIPTION OF THE INVENTION

In accordance with this invention there is provided a group of beta-carboline derivatives characterized by 2-piperazinyl-alkyl substitution of the beta-carboline nucleus. These compounds are antipsychotic agents and anxiolytic agents with minimal extrapyramidal side effects, useful in the treatment of psychological disorders such as paranoia and schizophrenia as well as general states of anxiety.

The compounds of this invention present the structural formula:

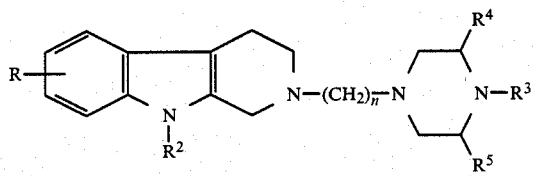

in which
R is hydrogen, halogen, hydroxy or alkyl of 1 to 6 carbon atoms;
$R^2$ is hydrogen, phenyl or substituted phenyl wherein said substituent is alkyl of 1 to 6 carbon atoms, alkoxy of 1 to 6 carbon atoms, halogen, trifluoromethyl, cyano or nitro;
$R^3$ is hydrogen or a moiety of the formula:

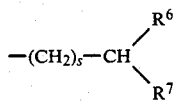

wherein
$R^6$ and $R^7$, independently, are phenyl or substituted phenyl in which said substituent is alkyl of 1 to 6 carbon atoms, alkoxy of 1 to 6 carbon atoms, halogen, trifluoromethyl, cyano or nitro, and when
$R^6$ and $R^7$ are taken together they form a heterocylic moiety of the formula

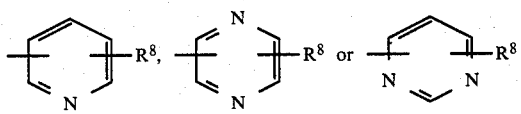

wherein
$R^8$ is hydrogen, alkyl of 1 to 6 carbon atoms, alkoxy of 1 to 6 carbon atoms, halogen, cyano or nitro; and
s is an integer from 0 to 7;
$R^4$ and $R^5$ are hydrogen or alkyl of 1 to 6 carbon atoms; and
n is an integer from 1 to 7;
or a pharmaceutically acceptable salt thereof.

Preferred among the compounds embraced by the foregoing genus are those
in which
R is hydrogen or a halogen (most preferrably fluorine);
$R^2$ is hydrogen;
$R^3$ is one of the depicted nitrogen heterocyclic groups where $R^8$ is hydrogen or a halogen; and
n is 3;
or a pharmaceutically salt thereof.

In the preceding descriptions of the compounds of this invention, the term, "halogen" is intended to embrace chlorine, bromine and fluorine and the pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The compounds of this invention are prepared by conventional methods whereby an appropriately substituted beta-carboline is alkylated with a dihaloalkane and the N-(ω-halo-alkyl)-β-carboline is coupled to appropriately substituted piperazine. The reactants employed are either commercially available or prepared by methods well within the skill of the medicinal chemist.

The antipsychotic properties of the compounds of this invention were established by standard pharmacologically accepted procedures involving conditioned avoidance studies in which trained male CD rats (Charles River), 400–450 gm body weight are exposed to a fifteen second warning tone (conditioned stimulus) continued for an additional fifteen seconds accompanied by electric shock. The rat can avoid the electric shock by depression of a response lever (lever-response). A response during the initial warning tone is considered an avoidance response. The avoidance response is determined and expressed as a percentage of total trials from an appropriate number of trials and a 50% block in avoidance responding ($AB_{50}$) is obtained from a dose-effect regression line. All the data is based upon (mg/kg) dosing of the animals.

As a measure of extrapyramidal side effects, the compounds of this invention were studied as antagonists of apomorphine-induced stereotyped behavior wherein CF-1 mice (Charles River) receive the test compound i.p. (six mice per dose level) and thirty minutes later receive 10 mg/kg apomorphine s.c. Five minutes after injection, the rearing-head-bobbing-licking syndrome induced by apomorphine is evaluated as present or absent for each animal. Readings are repeated every five minutes during a thirty minute test session. An $ED_{50}$ value (with 95% confidence intervals) is calculated for inhibition of apomorphine-induced stereotyped behavior by simple linear regression analysis. The compounds of this invention were inactive in this study. Thus, the compounds of this invention demonstrate a low potential for side-effects attending long term treatment with such standard antipsychotic drugs as haloperidol and chlorpromazine.

In further support of the low potential for side-effects exhibited by the compounds of this invention, the compounds were tested in accordance with a modification of the procedure of Fields et al., Brain Res., 136, pp. 578–584 (1977) and Yamamura et al., eds., Neurotransmitter Receptor Binding, Raven Press, N.Y. (1978), wherein homogenized limbic brain tissue is incubated with $^3$H-spiroperidol and various concentrations of test compound, filtered and washed and shaken with Hydrofluor scintillation cocktail (National Diagnostics) and counted in a Packard 460CD scintillation counter. Binding in the presence of the test compound is expressed as a percent of specific binding (total binding less binding in the presence of 1 μM (+)butaclamol). An inhibition constant ($K_i$) is calculated for each test compound to catagorize its limbic D-2 binding potential. The larger the number, the less potential for dopamine receptor binding and attendant side effects from administration of the antipsychotic agent. Inhibition constants (95% confidence interval) for standard antipsychotics are:

haloperidol—4.0(3.0–5.6)nM;
clozapine—34(23–54)nM;
fluphenazine—4.5(3.6–5.6)nM; and
sulpiride—376(174–5000)nM The compounds of this invention are inactive in antagonizing apomorphine-induced stereotyped behavior and are effective in blocking avoidance responding upon i.p. administration in the condition avoidance lever response test procedure. For example, the compound of Example 1 showed blockage in avoidance at $AB_{50}=34.72$. The limbic D-2 binding test procedure demonstrated $K_i=574$ nM, 143 nM and 38 percent ($K_i>5$ μM) for the compounds of Examples 1–3, respectively.

From these data, the activity profile of the compounds of this invention are seen to be that of antipsychotic agents with much lower potential for extra-pyramidal side effects such as attend the use of major tranquillizers (sedation, pseudoparkinsonism, ataxia, muscle relaxation, etc.). This activity profile resembles that of the anxiolytic compound, buspirone.

Hence, the compounds of this invention are antipsychotic agents and anxiolytic agents useful in the treatment of psychoses such as paranoia and schizophrenia and in alleviating anxiety. As such, they may be administered neat or with a pharmaceutical carrier to a patient in need thereof. The pharmaceutical carrier may be solid or liquid.

A solid carrier can include one or more substances which may also act as flavouring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis or state of anxiety and the size, age and response pattern of the patient.

The following exaples illustrate the production of compounds of this invention.

EXAMPLE 1

2,3,4,9-Tetrahydro-2-[3-[4-(2-pyrimidinyl)-1-piperazinyl]propyl]-1H-pyrido[3,4-b]indole To a stirred solution of 2,3,4,9-tetrahydro-pyrido[3,4-b]indole (1.72 g, 0.01 mol) in 50 mL of dimethylformamide was added 2 mL of triethylamine. The reaction mixture was stirred for ½ hour and to this was added 2.3 g (0.015 mol) of 1-bromo-3-chloropropane. The reaction was stirred for 24 hours, the dimethylformamide was removed under reduced pressure and the residue was extracted 3×200 mL of methylene chloride. The methylene chloride extracts were collected, washed with water and dried over anhydrous sodium sulfate.

Evaporation of the methylene chloride afforded 2 g (83% yield) of 2,3,4,9-tetrahydro-2-(3-chloropropyl)-1H-pyrido[3,4-b]indole as a thick red oil. This chloropropyl derivative was dissolved in 50 mL of dimethylformamide and while stirring 2 mL of triethylamine and 1.3 g (0.008 mol) of 1-(2-pyrimidyl)piperazine was addd. The reaction mixture was stirred for 48 hours. Dimethylformamide was removed under reduced pressure and the residue was extracted with 2×200 mL of methylene chloride. The methylene chloride extracts were collected, dried over anhydrous sodium sulfate and removed under reduced pressure. The separated oil was dissolved in ethanol and was converted to the trihydrochloride salt; mp. 238°–240° C.

Analysis for: $C_{22}H_{28}N_6\cdot 3HCl\cdot 1\frac{1}{2}H_2O$ Calculated: C, 50.62; H, 6.63; N, 16,39; Cl, 20.78; Found: C, 50.78; H, 6.59; N, 16.84; Cl, 19.06.

EXAMPLE 2

2-[3-[4-[bis(4-Fluorophenyl)methyl]-1-piperazinyl]-propyl]-2,3,4,9-tetrahydro-1H-pyrido[3,4-b]indole The title compound was prepared following the procedure of Example 1 with the exception that 1-bis(4-fluorophenylmethyl)piperazine was used instead of 1-(2-pyrimidinyl)piperazine. The product was converted to the trihydrochloride salt; mp. 218°–220° C.

Analysis for: $C_{31}H_{34}N_4F_2\cdot 3HCl\cdot 2H_2O$ Calculated: C, 57.57; H, 6.3; N, 8.67; Cl, 16.4; Found: C, 57.89; H, 5.81; N, 8.78; Cl, 16.06.

EXAMPLE 3

2-[3-(trans-3,5-Dimethyl-1-piperazinyl)propyl]-2,3,4,9-tetrahydro-1H-pyrido[3,4-b]indole The title compound was prepared following the procedure of Example 1 with the exception that cis-2,6-dimethylpiperazine was used instead of 1-(2-pyrimidinyl)piperazine. The product was converted to the trihydrochloride salt; mp. 248°–250°. C.

Analysis for: $C_{20}H_{30}N_4\cdot 3HCl\cdot H_2O$ Calculated: C, 52.92; H, 7.71; N, 12.34; Cl, 23.48; Found: C, 52.79; H, 7.46; N, 11.79; Cl, 22.46.

What is claimed is:

1. A compound of the formula:

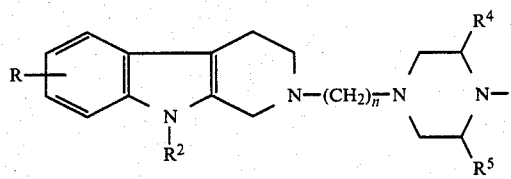

in which
R is hydrogen, halogen, hydroxy or alkyl of 1 to 6 carbon atoms;
$R^2$ is hydrogen, phenyl or substituted phenyl wherein said subsstituent is alkyl of 1 to 6 carbon atoms, alkoxy of 1 to 6 carbon atoms, halogen, trifluoromethyl, cyano or nitro;
$R^3$ is hydrogen or a moiety of the formula:

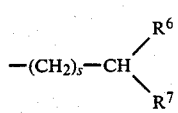

wherein
$R^6$ and $R^7$, independently, are phenyl or substituted phenyl in which said substituent is alkyl of 1 to 6 carbon atoms, alkoxy of 1 to 6 carbon atoms, halogen, trifluoromethyl, cyano or nitro, and when $R^6$ and $R^7$ are taken together they form a heterocyclic moiety of the formula:

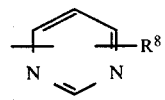

wherein
$R^8$ is hydrogen, alkyl of 1 to 6 carbon atoms, alkoxy of 1 to 6 carbon atoms, halogen, cyano or nitro, and
s is an integer from 0 to 7;
$R^4$ and $R^5$ are hydrogen or methyl; and
n is an integer from 1 to 7;
or a pharmaceutically acceptable salt thereof.

2. A compound of claim 1 of the formula:

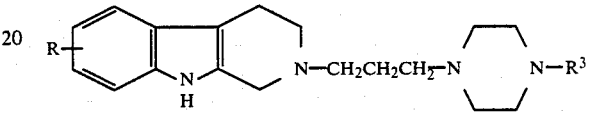

in which
R is hydrogen or a halogen; and
$R^3$ is

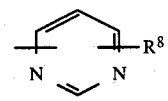

wherein $R^8$ is hydrogen or halogen; or a pharmaceutically acceptable salt thereof.

3. A compound of claim 1 of the formula:

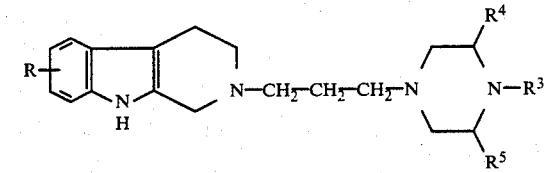

in which
R is hydrogen or a halogen;
$R^3$ is hydrogen, bis(4-fluorophenyl)-methyl or 2-pyrimidinyl;
$R^4$ and $R^5$ are hydrogen or methyl;
or a pharmaceutically acceptable salt thereof.

4. A compound of claim 1 of the formula 2,3,4,9-tetrahydro-2-[3-[4-(2-pyrimidinyl)-1-piperazinyl]propyl]-1H-pyrido[3,4-b]indole or a pharmaceutically acceptable salt thereof.

5. A compound of claim 1 of the formula 2-[3-[4-[bis(4-fluorophenyl)methyl]-1-piperazinyl]propyl]-2,3,4,9-tetrahydro-1H-pyrido[3,4-b]indole or a pharmaceutically acceptable salt thereof.

6. A compound of claim 1 of the formula 2-[3-(trans-3,5-dimetyl-1-piperazinyl)propyl]-2,3,4,9-tetrahydro-1H-pyrido[3,4-b]indole or a pharmaceutically acceptable salt thereof.

* * * * *